United States Patent [19]

Giersch et al.

[11] 4,375,866
[45] Mar. 8, 1983

[54] SKIN CLIP APPLIER

[75] Inventors: Robert V. Giersch, Raleigh; Douglas K. Hoeppner, Apex; William D. Webb, Cary, all of N.C.

[73] Assignee: Edward Weck & Company, Inc., Research Triangle Park, N.C.

[21] Appl. No.: 227,569

[22] Filed: Jan. 22, 1981

[51] Int. Cl.³ .......................... A61B 17/12; B25C 5/02
[52] U.S. Cl. ............................ 227/19; 72/410; 128/337; 227/85; 227/144; 227/DIG. 1
[58] Field of Search ................ 227/19, 85, 99, 120, 227/143, 144, DIG. 1; 128/334 R, 335, 337; 411/457, 458, 460, 470–473; 72/409, 410; 29/243.56

[56] References Cited

U.S. PATENT DOCUMENTS

| 2,767,400 | 10/1956 | Haberstump | 227/DIG. 1 |
| 3,777,355 | 12/1973 | Cooke | 72/410 X |
| 4,043,504 | 8/1977 | Hueil et al. | 227/120 X |
| 4,179,057 | 12/1979 | Becht et al. | 227/19 |
| 4,246,903 | 1/1981 | Larkin | 29/243.56 X |

Primary Examiner—Gil Weidenfeld
Assistant Examiner—Fred A. Silverberg
Attorney, Agent, or Firm—Lawrence S. Levinson; John J. Archer

[57] ABSTRACT

A skin clip applier for placing skin clips to close a wound comprises a handle assembly including an actuating element and a cartridge assembly adapted to be affixed to said handle assembly and including skin clip-deforming jaw elements which are actuated by operation of the handle assembly to place and deform preformed skin clips, delivered individually to said deforming jaws, to close a wound.

7 Claims, 9 Drawing Figures

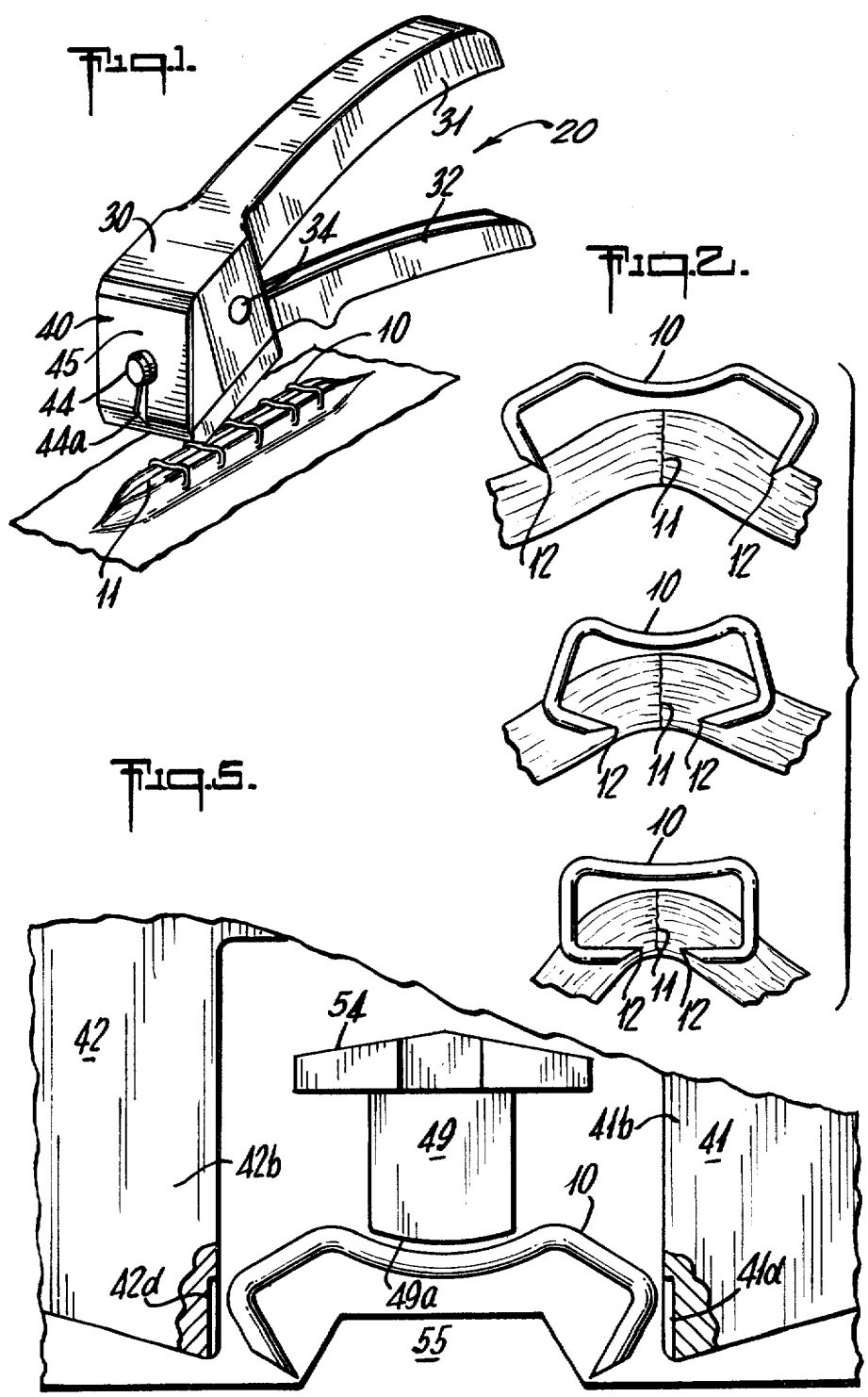

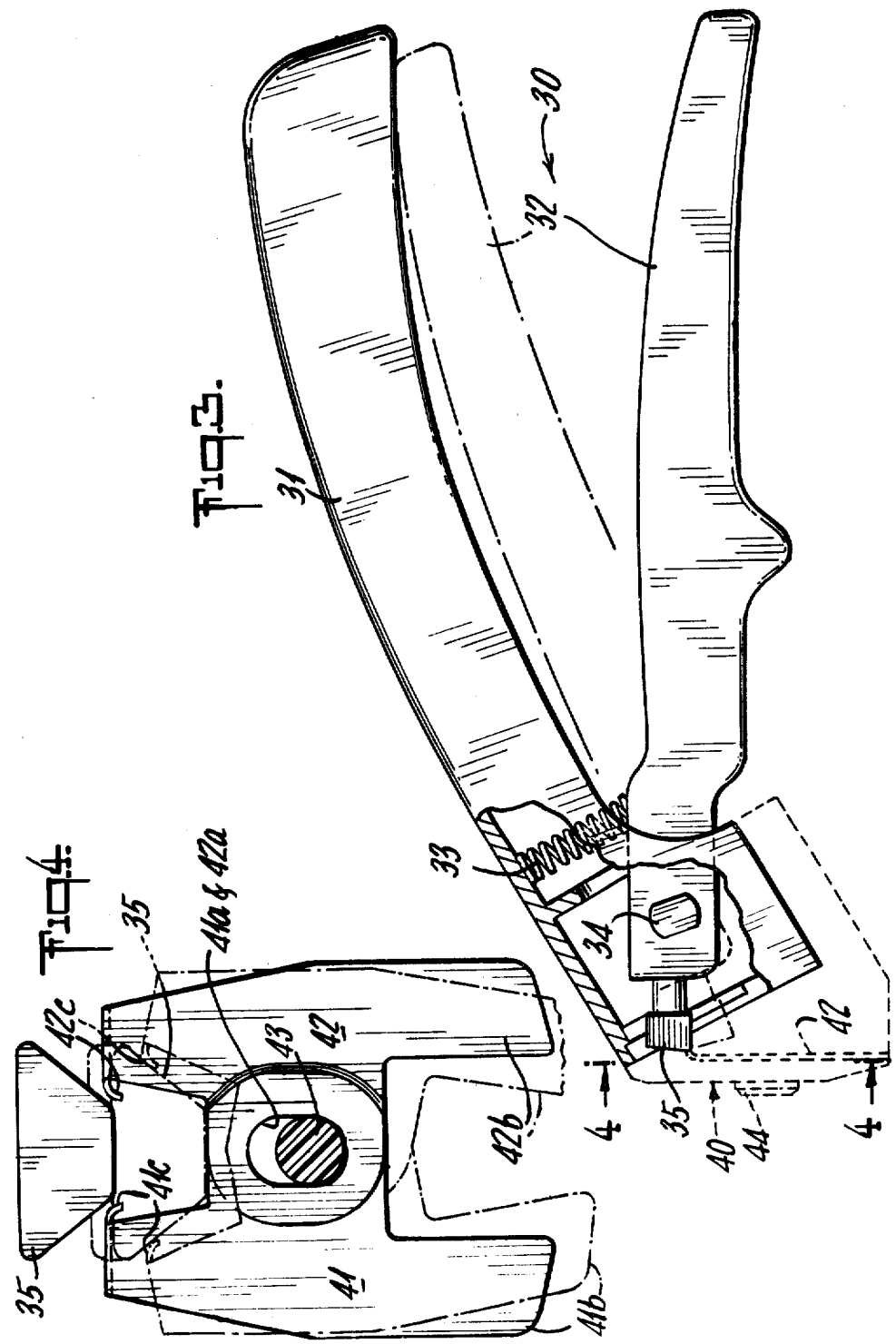

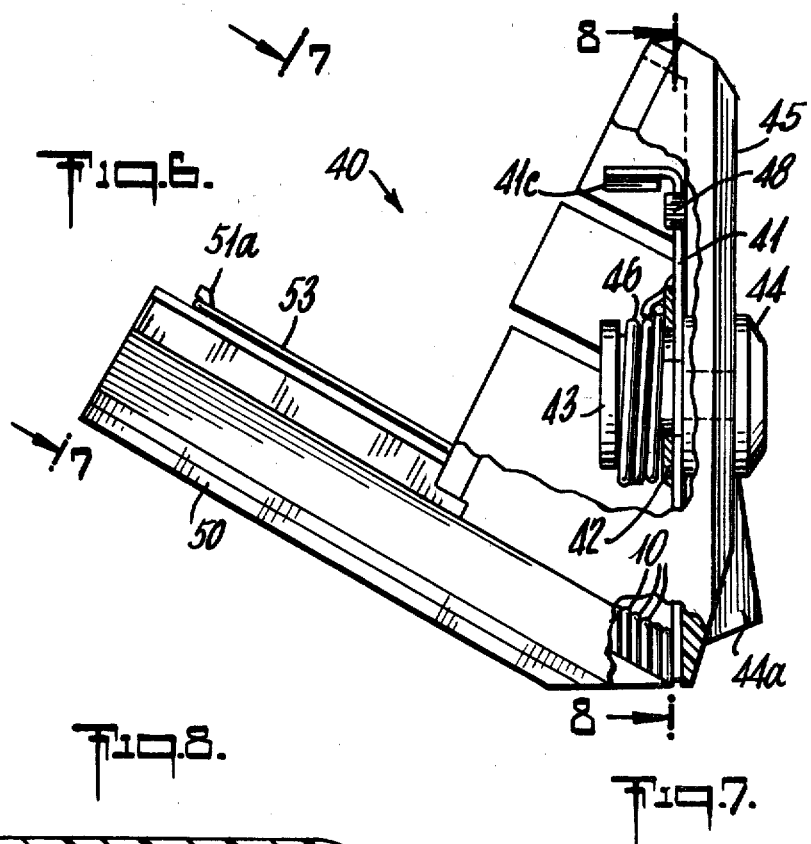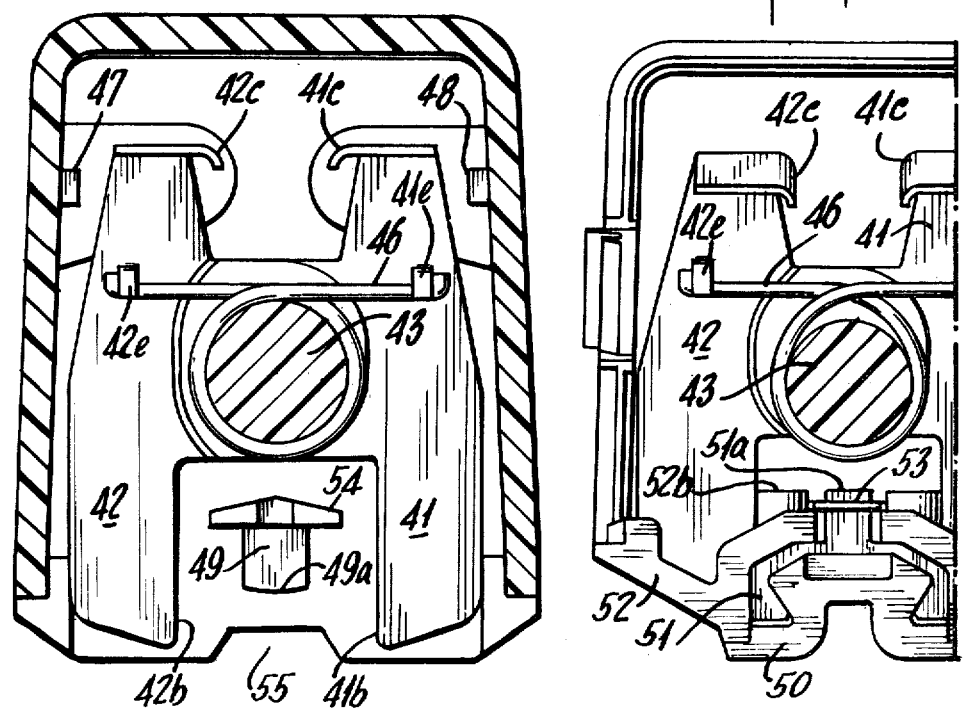

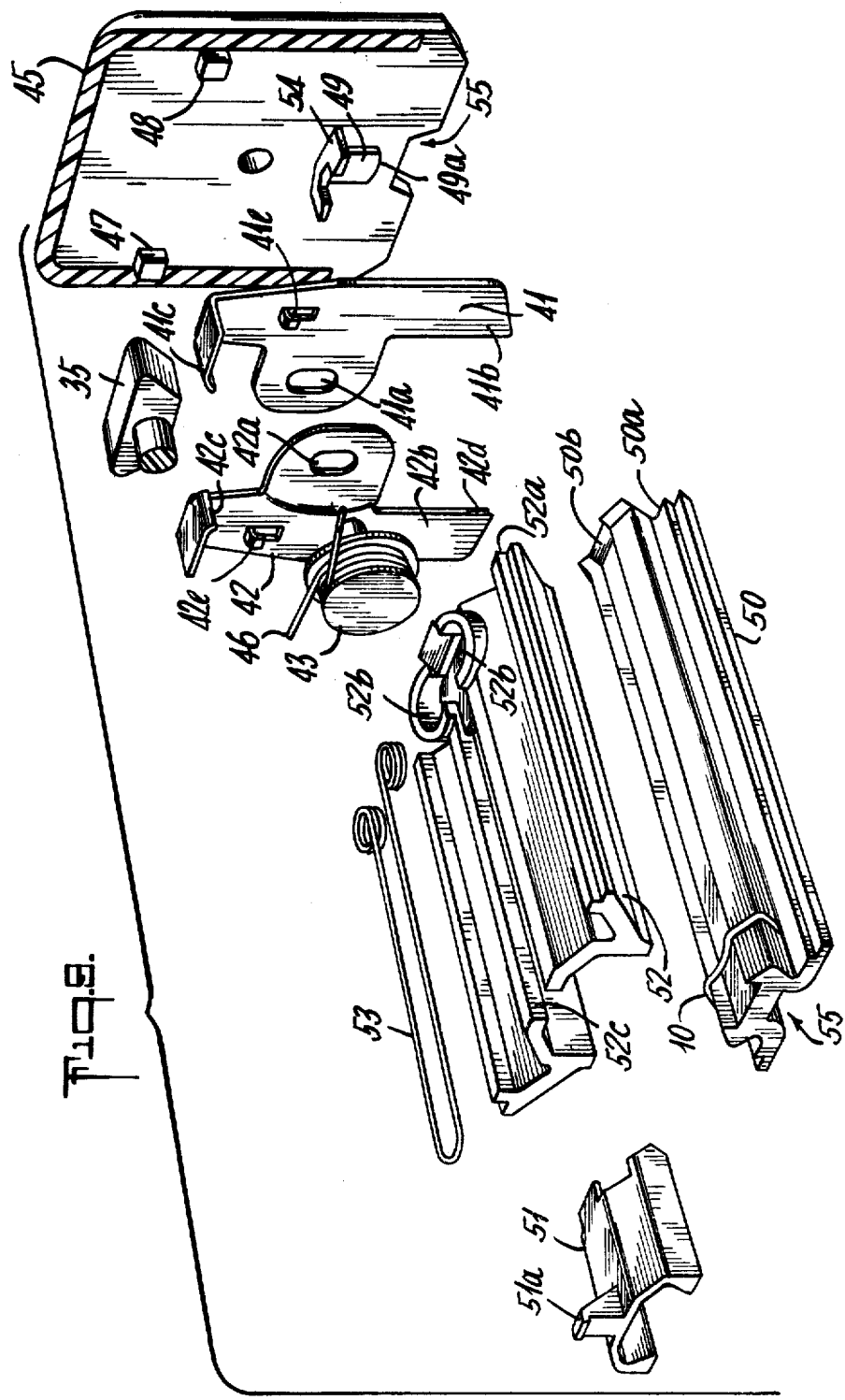

SKIN CLIP APPLIER

FIELD OF THE INVENTION

This invention relates to a skin clip applier useful for placing skin clips or staples into the skin across a wound to close the wound and to retain it in a closed and healing position.

BACKGROUND OF THE INVENTION

Whenever it is necessary to close an incision or a wound, whether at the completion of a surgical procedure or to repair accidental damage, it is becoming more and more common for the attending surgeon to choose to use metal skin clips or staples instead of thread sutures. This has become true with the development of stapling devices, or skin clip appliers, particularly suited for surgical use and the consequent speed with which incision or wound closure can be accomplished by the surgeon with such devices as compared to the use of thread suture materials with needles and the required time-consuming tying of the suture material. See, for example, U.S. Pat. Nos. 3,643,851 and 3,717,294 which describe skin staplers and U.S. Pat. No. 4,014,492 which describes a particular type of staple. When staples or skin clips are used for incision or wound closure, they are removed with a special removal tool or extractor such as disclosed in U.S. Pat. No. 4,026,520, or an adaption of the staple remover, originally designed for removal of staples from paper or like material, shown in U.S. Pat. No. 2,202,984.

BRIEF SUMMARY

The skin clip applier of the present invention overcomes disadvantages of prior skin clip appliers or stapling devices which results in an improvement in the speed and accuracy with which skin clips may be placed to close an incision or a wound and an improved shape of the skin clip when deformed into place as an incision or a wound closing element by the present skin clip applier. Such improved shape of the placed skin clip results in considerably less trauma to the patient when the skin clip is removed. The specific advantages of the present skin clip applier as compared to prior devices will be explained more fully in the following detailed description of an illustrative specific embodiment of the invention.

The skin clip applier of this invention is formed of a combination of a handle assembly and a cartridge assembly which may be adapted to fit together so that an empty cartridge may be removed and replaced with a cartridge full of performed skin clips. The closing action of the handle assembly functions to actuate a pair of jaws in the cartridge assembly and deform into place as a wound closing element a preformed skin clip which is fed between the jaws as the leading one of a plurality of skin clips pre-loaded into the cartridge assembly on a clip carrier and moved toward and between the pair of jaws by the action of a clip pusher which is biased toward the jaws. The pair of jaws are pivoted on a single stud, preferably with elongated pivot holes in each jaw to provide limited movement toward and away from the surface of the skin into which a skin clip is to be placed. Such movement permits the points of the skin clip to be placed into the skin before actual deformation of the skin clip begins and assists in the approximation and closure of the incision or wound.

BRIEF DESCRIPTION OF THE DRAWINGS

The skin clip applier of this invention will be described in more detail with reference to the accompanying drawings which show one illustrative specific embodiment of the invention.

In the drawings:

FIG. 1 is a perspective view of the skin clip applier approximately in the position of use after having placed skin clips to close an incision.

FIG. 2 shows three steps in the deformation by the skin clip applier of a single skin clip which is being placed to close an incision or a wound.

FIG. 3 is a side view of the handle of the skin clip applier partly in section.

FIG. 4 is a section of the cartridge taken along line 4—4 of FIG. 3.

FIG. 5 is an enlarged partial view of the applier showing the skin clip in position between the jaws of the skin clip applier just prior to actual deformation.

FIG. 6 is a side view partly in section of the cartridge assembly.

FIG. 7 is a view partly in section of the cartridge taken along line 7—7 of FIG. 6.

FIG. 8 is a section of the cartridge taken along line 8—8 of FIG. 6.

FIG. 9 is a perspective and exploded view showing the relation of parts of the cartridge assembly to the actuating element of the handle assembly.

DETAILED DESCRIPTION

With reference to the accompanying drawings, the same parts are identified by the same reference numerals in all figures.

In FIG. 1, a specific embodiment of the skin clip applier of the present invention, indicated generally by reference numeral 20, is shown in an attitude of use after having placed five skin clips 10 to close a wound or an incision 11. The skin clip applier 20 includes a handle assembly 30 and a cartridge assembly 40 which are detachable one from the other.

It is to be understood, however, that the skin clip applier of this invention may have a handle assembly and cartridge assembly incorporated into a unitary device rather than as detachable elements.

FIG. 2 (three views) shows a skin clip 10 in progressive stages of deformation during the placing of the skin clip 10. In the first view, the points 12 of the skin clip 10 have just punctured the skin as the bottom edge of the cartridge assembly 40 of the skin clip applier 20 is brought into contact with the incision or wound 11. At this stage the deformation of the skin clip 10 has not actually begun, but the skin clip 10 is held in a position, as will be explained in more detail hereinafter, such that the points 12 extend below the bottom edge of the cartridge assembly 40 to permit contact with and penetration of the skin to maintain the approximation of the wound or incision site. In the second view, the skin clip 10 has been partially deformed and the points 12 of the skin clip 10 have substantially completed their penetration to hold the wound or incision 11 in a closed position. In the third view, the skin clip 10 is fully deformed and placed to hold the wound or incision together. It should be noted here that the fully deformed skin clip 10 is holding the wound or incision 11 closed in a butted relationship. If desired, the wound may be approximated in a slightly everted attitude and the skin clips 10 applied. In either procedure, the top of the skin clip 10 is not touching but is slightly separated from the wound or incision 11, and the top of the skin clip 10 is bowed downwardly to a slight extent, i.e., it has not been deformed to a point that the top of the skin clip 10 is absolutely straight. Both of these conditions are important from the standpoint of patient comfort both in case of any swelling of the wound or incision site 11 and the subsequent removal of the skin clips 10, and both conditions are brought about by the action of the skin clip applier 20.

The handle assembly 30, as shown in FIG. 3, includes a frame 31, a handle 32, a compression spring 33, a pivot axle 34, and a cam 35. The frame 31 and handle 32 are connected through the pivot axle 34 so that the gripping end of the handle 32 is permitted to move about the pivot axle 34 into contact with (dotted outline) and away from (solid outline) the frame 31. On the opposite end of the handle 32, i.e., on the other side of pivot axle 34 and at the extreme end, the cam 35 is attached and is the actuating element of the handle assembly 30 which cooperates with those elements of the cartridge assembly 40 which actually deform a skin clip 10 during placement of the skin clip 10. The compression spring 33 is present to bias the handle 32 in the open position, i.e., with the gripping portion at its most remote position from the frame 31. The open end or pivot axle 34 end of the frame 31 is shaped to receive the cartridge assembly 40 therein in such a manner that the cam 35 is positioned within the cartridge assembly 40 in order to be in engagement with certain elements therein as will be explained in detail hereinafter.

The cartridge assembly 40 is shown in detail in FIGS. 4 through 9 which illustrate the various elements of the cartridge assembly 40 and how such elements function to present and deform a skin clip 10 when actuated by the downward movement of cam 35 as the result of closing the handle 32 into virtual contact with the frame 31 when the surgeon closes his hand while gripping the frame 31 and handle 32 of the handle assembly 30 of the skin clip applier 20.

The cartridge assembly 40 includes jaws 41 and 42 pivoting on stud 43 which is fastened into front plate 45. The hub 44 shown on the front plate 45 is not a required element but is present simply to provide a more substantial bulk of material into which the stud 43 can be fastened. Jaws 41 and 42 are formed with elongated holes 41a and 42a which fit over stud 43 and provide for limited vertical motion of the jaws 41 and 42 as will become apparent from the subsequent description. Torsion spring 46 is mounted on and around stud 43 after the jaws 41 and 42 are placed thereon. One free end of torsion spring 46 is attached to jaw 41 at 41e and the other free end is attached to jaw 42 at 42e in a manner such that the jaws 41 and 42 are biased both in the uppermost position permitted by the elongated holes 41a and 42a and in an open position, i.e., the deforming surfaces 41b and 42b are at their most separated position and the cam bearing surfaces 41c and 42c are at their closest position. The deforming surfaces 41b and 42b must move in the same plane, and the cam bearing surfaces 41c and 42c most conveniently move in the same plane. Consequently, one of the jaws is offset sufficiently to move the deforming surface and the cam bearing surface into line with those of the other jaw. With the cartridge assembly 40 connected to the handle assembly 30, when cam 35 is moved from its extreme biased position to its opposite limited position by the closing of the handle 32 to or into the frame 31, the specifically shaped undersurface of cam 35 contacts the cam bearing surfaces 41c and 42c of jaws 41 and 42 and smoothly moves these surfaces 41c and 42c down and apart, as best illustrated in FIG. 4. As a consequence of this movement of cam bearing surfaces 41c and 42c, the whole bodies of the jaws 41 and 42 are moved down to the limit provided by the elongated holes 41a and 42a and the deforming surfaces 41b and 42b move into skin clip deforming relation. Stops 47 and 48 are provided in the form of bosses on the inside surface of front plate 45 to limit the movement of jaws 41 and 42 to prevent excess deformation of skin clip 10.

As the deforming surfaces 41b and 42b are moved toward each other by the action of cam 35 when the handle is being closed, the skin clip 10 positioned therebetween (as best illustrated in FIG. 5) will be deformed through the stages illustrated in FIG. 2. During such deformation of skin clip 10, it is held in proper position with the aid of grooves or coining slots 41d and 42d in the deforming surfaces 41b and 42b and the upward movement of skin clip 10 as it is deformed is limited by the stop 49 which is shown as a boss on the inside surface of front plate 45 but may be provided elsewhere, as for example, on the forward end of carrier cover 52. The surface 49a of stop 49 is curved to fit the arcuate shape of the top of skin clip 10 and this assists in maintaining a slight downward bow in the top of the skin clip 10 when it is fully deformed as shown in the third and last view of FIG. 2. As explained previously, this slight downward bow in the top of the fully deformed skin clip 10 is an important feature from the standpoint of patient comfort, particularly during the removal of skin clip 10.

The skin clip delivery system forming a part of the cartridge assembly 40 includes a skin clip carrier (or slide) 50, a skin clip pusher 51, a skin clip carrier cover 52, and a biasing spring 53 to bias the skin clip pusher 51 and thereby the skin clips 10 on carrier 50 toward the front plate 45 and the deforming jaws 41 and 42. Skin clip carrier 50 forms the bottom of the cartridge assembly 40 and carrier cover 52 fits over carrier 50 to provide a passageway for the skin clips 10 and skin clip pusher 51 and prevent any binding of skin clip pusher 51 on carrier 50. Carrier cover 52 includes a slot 52c to permit passage of the skin clip pusher boss 51a. The forward ends 50a and 52a of the carrier 50 and carrier cover 52 abut and are fastened to front plate 45 to form the major portion of the cartridge assembly 40. Skin clips 10 are loaded onto carrier 50 and skin clip pusher 51 is then placed on the carrier 50. Biasing spring 53, preferably a constant force spring such as a saddle spring, is then affixed to the forward end 52a of carrier cover 52 and to skin clip pusher 51. As shown in FIG. 9, the free ends in coil form of spring 53 are placed in the spring wells 52b of carrier cover 52 and the loop or middle of the spring 53 is placed around the boss 51a of the skin clip pusher 51 to bias the skin clips 10 toward the deforming jaws 41 and 42. A specially shaped boss 54 on the inside wall of front plate 45 provides a partial cover for the spring wells 52b and thereby retains the ends of spring 53 therein.

In FIG. 9, a clip 10 is shown resting on the carrier 50 which is shaped to conform to the preformed clip 10. When contacted by the angled (about 30° as shown) forward face or contact surface of the pusher 51, the clip 10 will assume an angled position on carrier 50 (as most clearly shown in FIG. 6) such that the clip 10 is at all times parallel to the inside surface of the front plate 45 and the plane of deforming movement of the jaws 41 and 42. The forward end of skin clip carrier 50 is provided with a lift 50b which serves to prevent the clips 10 from sliding off the forward end of carrier 50 and also locates or positions each clip 10 so that it is properly presented to the deforming jaws 41 and 42.

The bottom of front plate 45 and the bottom of skin clip carrier 50 are cut out to provide a channel 55 slightly wider than a deformed skin clip 10 to permit the skin clip applier 20 to pass over the everted wound and any skin clips implanted in the wound.

As shown in FIGS. 1 and 6, the front plate 45 may be provided with a positioning guide 44a to assist in the accurate placing of the skin clips 10.

The skin clip applier of the present invention is simple and sturdy in construction and functions to place skin clips in a wound or incision closing site in a manner that results in a minimum of patient discomfort because it provides room for any swelling of the site and results in a shape of placed skin clip which can be removed with the least trauma. This latter result is accomplished because of the slight downward bow of the top of the skin clip (as shown in the third view of FIG. 2) which minimizes rotation or warping of the skin clip by the customary removal tool or extractor, and consequently, during removal it minimizes any distortion or scraping by the withdrawing pointed legs of the skin clip of the entry holes formed by the pointed legs during placement of the skin clip. The downward bow of the skin clip placed by the skin clip applier of the present invention requires less force to deform during removal than the upward bow of those skin clips placed by other skin clip appliers. Skin clip appliers or staplers which utilize an anvil about which a skin clip or staple is formed must of necessity have an upward bow to the top of such a skin clip because the anvil limits the deformation to a theoretical flat or straight top of such a skin clip, but in practice an upward bow will be present. Such upward bow has been found to occassionally cause warping and rotation during removal by the customary removal tools.

The skin clips used by the skin clip applier of the present invention are customarily of stainless steel, and 316L stainless steel is preferred. The skin clips are conventionally formed of stainless steel wire which may be of varying thickness, and the skin clips may be of various sizes. Because the skin clips used by the present applier are preformed into the particular shape described hereinbefore, a lesser force is required to deform the clip into its final woundclosing shape. This makes it possible to provide an applier the use of which is less tiring to the surgeon.

What is claimed is:

1. A skin clip applier comprising in combination a handle assembly and a skin clip cartridge assembly, said handle assembly comprising a handle pivotally connected within its length to a frame, means to bias one end of said handle away from said frame, a cam element attached to the opposite end of the handle and means for affixing the skin clip cartridge assembly in operative relation to said cam element of said handle assembly, said cartridge assembly comprising a skin clip delivery system adapted to present individual pre-formed skin clips serially to a pair of jaw elements pivotally mounted for deforming said skin clips, means to bias said deforming jaw elements away from each other, and means for affixing the handle assembly in operative relation to the jaw elements of said cartridge assembly to force said jaw elements into deforming relation to each of the skin clips, the handle and the cam element each having a longitudinal axis substantially perpendicular to the plane of said jaw elements.

2. A skin clip applier according to claim 1 wherein each of said pair of jaw elements has a pivot hole elongated to provide limited movement of said jaw elements to and away from a position of deformation of said skin clip by said jaw elements.

3. A handle assembly for a skin clip applier comprising a handle pivotally connected within its length to a frame, means to bias one end of said handle away from said frame, a cam element attached to the opposite end of the handle and means for affixing a skin clip cartridge assembly, including a pair of skin clip deforming jaw elements, in operative relation to said cam element of said handle assembly, the handle and the cam element each having a longitudinal axis substantially perpendicular to the plane of said jaw elements.

4. A cartridge assembly for a skin clip applier comprising a skin clip delivery system adapted to present individual pre-formed skin clips serially to a pair of jaw elements pivotally mounted for deforming said skin clips, means to bias said deforming jaw elements away from each other, and means for affixing an actuating handle assembly, including a handle and a cam element attached to said handle at a handle end adjacent to said jaw elements, in operative relation to the jaw elements of said cartridge assembly to force said jaw elements into deforming relation to each of the skin clips, the handle and the cam element each having a longitudinal axis substantially perpendicular to the plane of said jaw elements.

5. A cartridge assembly according to claim 4 wherein each of said pair of jaw elements has a pivot hole elongated to provide limited movement of said jaw elements to and away from a position of deformation of said skin clip by said jaw elements, and means to move said jaw elements to said position of deformation.

6. A skin clip applier comprising in combination a handle assembly and a skin clip cartridge assembly, said handle assembly comprising a handle pivotally connected within its length to a frame, means to bias one end of said handle away from said frame, and a cam element attached to the opposite end of the handle, said cartridge assembly being joined to said handle assembly in operative relation to said cam element of said handle assembly, said cartridge assembly comprising a skin clip delivery system adapted to present individual pre-formed skin clips serially to a pair of jaw elements pivotally mounted for deforming said skin clips, means to bias said deforming jaw elements away from each other, and means for affixing the handle assembly in operative relation to the jaw elements of said cartridge assembly to force said jaw elements into deforming relation to each of the skin clips, the handle and the cam element each having a longitudinal axis substantially perpendicular to the plane of said jaw elements.

7. A skin clip applier according to claim 6 wherein each of said pair of jaw elements has a pivot hole elongated to provide limited movement of said jaw elements to and away from a position of deformation of said skin clip by said jaw elements.

* * * * *